United States Patent [19]

Tokuyasu et al.

[11] 3,994,782
[45] Nov. 30, 1976

[54] METHODS FOR EXTRACTING AND PURIFYING KALLIDINOGENASE

[75] Inventors: Kiyochika Tokuyasu, Higashiyamato; Takeshi Yokobori, Sayama; Chizuko Nakahara, Hino, all of Japan

[73] Assignee: Seikagaku Kogyo Co. Ltd., Tokyo, Japan

[22] Filed: Dec. 5, 1975

[21] Appl. No.: 638,042

[52] U.S. Cl.............................. 195/66 R; 424/110
[51] Int. Cl.² .................. C07G 7/026; A61K 37/48
[58] Field of Search.............. 195/66 R, 65; 424/110

[56] References Cited
UNITED STATES PATENTS

| | | | |
|---|---|---|---|
| 3,660,237 | 5/1972 | Schultz.............................. | 195/66 R |
| 3,809,748 | 5/1974 | Khouw et al....................... | 424/110 |

*Primary Examiner*—Lionel M. Shapiro
*Attorney, Agent, or Firm*—Sherman & Shalloway

[57] ABSTRACT

A method for extracting and collecting kallidinogenase (EC 3.4.4.21 substance) which comprises extracting the pancreas of a mammal with water in the presence of a salt at a temperature of about 45° to about 60° C. and a pH of about 5 to about 8, wherein the extraction is carried out in the presence of a water-soluble salt of magnesium with an acid, and a method for purifying kallidinogenase which comprises subjecting the aqueous phase of a kallidinogenase-containing aqueous extract obtained from the pancreas of a mammal to an adsorption-elution treatment using an anion-exchange resin, wherein said aqueous phase of the kallidinogenase-containing aqueous extract is brought into contact with a gel-type weakly basic anion-exchange resin to cause the kallidinogenase fraction to be adsorbed to said resin, and the kallidinogenase is eluted with an aqueous solution of an ammonium salt of a weak acid, thereby to collect the kallidinogenase.

4 Claims, No Drawings

METHODS FOR EXTRACTING AND PURIFYING KALLIDINOGENASE

This invention relates to an improved method for extracting and collecting kallidinogenase (EC 3.4.4.21 substance, known as Kallikrein by trademark) from the pancreas of mammal.

The method of this invention affords improved kallidinogenase separability (increased yield) whereby a kallidinogenase-containing aqueous phase with reduced amounts of protein and other impurities (low turbidity) can be obtained in a greater amount than in prior art techniques using the same amount of extracting water. Furthermore, the kallidinogenase-containing aqueous phase having high kallidinogenase activity can be obtained with operational advantages by a simple solid liquid separating procedure without requiring any means of separating the aqueous phase, for example, centrifugal separation. According to this method, the kallidinogenase is very stable for heat under the extracting conditions of the invention as compared with the prior art techniques, and advantageously exhibits no likelihood of denaturation during the extracting step.

The present invention also relates to a method for purifying kallidinogenase in which kininase can be removed very easily and substantially completely.

It has already been known to extract kallidinogenase, a circulatory hormone, from the "pancreas of mammal" (as referred to in the present application) such as the pancreas itself of a mammal, a powder of the pancreas, or a kallidinogenase-containing extract of the pancreas, and to purify the extracted crude kallidinogenase.

The conventional technique of extracting kallidinogenase from the pancreas of mammal comprises subjecting pancreas having a high fat content to a fat removing treatment which however requires a complicated procedure, and then extracting the defatted pancreas with water at an elevated temperature at a pH of about 4 to about 7. When the fat-removing treatment is omitted in this technique, the extracting operation and the operation of separating and collecting the aqueous phase are extremely difficult. The method also has the defect that even after performing the fat removing treatment, the extracting operation and the aqueous phase-separating operation are still difficult, and the yield of kallidinogenase is low.

In an attempt to overcome the difficulties of this technique, an improved method was suggested in which the above extracting operation is carried out using an aqueous solution of an alkali metal salt such as sodium chloride or an ammonium salt in the co-presence of an organic solvent at a pH of 5.5 to 9.5 (see Japanese Patent Publication No. 17041/73). This suggestion is an improvement over the method in which no salts are used, but suffers from disadvantages arising from the use of organic solvents. It is desired to be improved further in regard to the yield (activity), heat stability, and turbidity of kallidinogenase during the extraction step.

On the other hand, various suggestions have been made in regard to the purification of a kallidinogenase-containing aqueous extract obtained from the pancreas of mammal by adsorption-elution techniques. For example, two types of purifying methods have been suggested, one type relying on the use of polysaccharide-type non-resinous materials which, for example, includes a method comprising allowing the crude kallidinogenase to be adsorbed to a weakly basic anion-exchange cellulose and separating it (Japanese Patent Publication No. 11697/62), and a method comprising adding a lead or zinc salt to an aqueous solution containing kallidinogenase, allowing the resulting kallidinogenase precipitate to be adsorbed to a weakly basic anion-exchange cellulose or cross-linked dextran (SEPHADEX: tradename) and separating it (Japanese Laid-Open Patent Publication No. 56889/73, the other type relying on the use of ion-exchange resins which, for example, includes a method comprising adding a protein precipitant to an extract of the gland tissue of the pancreas, allowing the resulting kallidinogenase to be adsorbed onto a macroporous strongly basic anion-exchange resin, and separating it (Japanese Laid-Open Patent Publication No. 103715/73).

The methods utilizing a polysaccharide-type non-resinous material, as adsorbent, have the disadvantage that the physical strength of the ion-exchange material is not sufficient, and contamination by microorganisms is liable to occur, and thus are not feasible for commercial operations. On the other hand, the other type has the advantage of avoiding the above-mentioned troubles, but is still unsatisfactory in regard, for example, to the elution of the desired product and the removal of undesirable kininase.

We made extensive investigations in order to remove the defects of the conventional methods for extracting and collecting kallidinogenase and the conventional methods for purifying the kallidinogenase extract. As a result, we found that kallidinogenase can be separated and collected with superior heat stability, separability, turbidity and activity by extracting the pancreas of mammal with water in the presence of a water-soluble salt formed between magnesium, which is a metal of period 3 of Group II of the periodic table, and an acid. As will be shown later by comparative experiments, it has been found that according to the method of this invention, better results can be achieved than in the case of using the alkali metal salts or ammonium salts indicated above with regard to the prior art techniques, and that the improvement attained by this invention cannot be achieved even when salts of calcium, a metal of period 4 of Group II of the periodic table, or aluminum, a metal of Group III of the periodic table, are used.

Furthermore, we found that by utilizing a gel-type weakly basic anion-exchange resin, a greater part of the undesirable kininase can be removed completely in a washing step after adsorption, and the adsorbed kallidinogenase can be eluted and recovered with good efficiency and at good recovery ratios by a subsequent eluting step which is less time-consuming than in the prior art. It has also been found that this superior purification effect is not obtained by using a gel-type strongly basic anion-exchange resin or a macroporous weakly basic anion-exchange resin, but is a unique effect obtainable only with the gel-type weakly basic anion-exchange resin.

Accordingly, it is an object of this invention to provide a superior improved method for extracting and collecting kallidinogenase from the pancreas of mammal.

Another object of this invention is to provide a superior improved method for purifying a kallidinogenase-containing aqueous extract obtained from the pancreas of mammal thereby to obtain purified kallidinogenase.

Other objects and advantages of this invention will become apparent from the following description.

According to this invention, there is first provided a method for extracting and collecting kallidinogenase which comprises extracting the pancreas of mammal with water in the presence of salts at a temperature of about 45° to about 65° C. and a pH of about 5 to about 8, wherein the extraction is carried out in the presence of a water-soluble salt formed between magnesium and an acid.

The pancreas of mammal used in this invention may be an attenuated or minced product of the raw pancreas of mammal such as pig, cow, horse or whale, or an acetone-treated pancreas powder or a water-extract of the pancreas. In the present invention, it is not necessary to subject the raw pancreas to a complicated defatting treatment in advance, but the raw pancreas, attenuated to a desired form to allow easy extraction, can be used directly.

According to the method of this invention, the pancreas of mammal is extracted with the water-soluble magnesium salt of an acid added. The extraction is carried out at a temperature of about 45° to about 60° C. at a pH of about 5 to about 8 for a period of, say, about 30 minutes to about 2 hours. When the pH is less than about 5 or more than about 8, the kallidinogenase is liable to be deactivated during the extracting operation, or the separability of the aqueous phase becomes poor to cause a reduction in the yield of kallidinogenase and moreover, the separating operation becomes difficult. When the extracting temperature is less than about 45° C., the separability of the aqueous phase becomes poor, and long periods of time are required for separation by, for example, allowing the system to stand. This results in the deactivation of the kallidinogenase and its reduced yield. On the other hand, when the extracting temperature exceeds about 60° C., the kallidinogenase is liable to be deactivated, and this tendency is likely to increase unless the time required for separating the kallidinogenase by allowing the system to stand is shortened. However, the shortening of the separating time makes the separation insufficient, and causes a reduction in the yield of kallidinogenase.

The extraction in accordance with the method of this invention is carried out in the presence of a water-soluble salt of magnesium with an acid, which has been added to the extraction system. The water-soluble magnesium salt of an acid may, for example, be salts formed between magnesium and acids such as mineral acids, carbonic acid, and fatty acids containing 1 to 5 carbon atoms. Specific examples of the water-soluble magnesium salts are magnesium carbonate, magnesium chloride, magnesium nitrate, magnesium sulfate, magnesium formate, magnesium acetate, magnesium propionate, magnesium butyrate, magnesium lactate, magnesium malate, magnesium oxalate, magnesium succinate, and magnesium valerate.

The extracting method of this invention makes it possible to afford a kallidinogenase with superior heat stability, separability, turbidity and kallidinogenase activity as compared with the case of using alkali metal salts or ammonium salts as previously suggested and also in the case of using similar salts of calcium (a metal of Group II of the periodic table) or of aluminum (a metal of period 3, Group III of the periodic table). These advantages of this invention can be demonstrated experimentally as follows:

The experimental procedure comprises adding 500 ml. of water to 100 g of minced raw pancreas (the essential pancreas content: about 50%) of pig, adjusting the pH of the mixture to 6, adding each of the various salts shown in Table 1, allowing the mixture to stand for 1 hour at 55° C. to extract and collect kallidinogenase. The separability, turbidity and relative kallidinogenase activity of the kallidinogenase-containing aqueous extract, and the heat stability of kallidinogenase are determined. The results are shown in Table 1.

Table 1

| | Salts | Concentration of salts (M) | Kallidinogenase-containing aqueous extract | | | Heat-stability of kallidinogenase (relative residual activity, %) |
| | | | Separability (%) | Turbidity (O.D.600) | Relative kallidinogenase activity (%) | |
| --- | --- | --- | --- | --- | --- | --- |
| Comparison | Not added | | 57 | 3.1 | 60 | 77 |
| | ammonium chloride | 0.03 | 65 | 1.7 | 68 | 70 |
| | Sodium acetate | 0.03 | 60 | 1.7 | 75 | 83 |
| | Sodium chloride | 0.03 | 72 | 1.7 | 88 | 86 |
| | Sodium chloride | 0.06 | 70 | 1.6 | 88 | 86 |
| | Sodium sulfate | 0.03 | 60 | 1.7 | 70 | 75 |
| | Aluminum acetate | 0.03 | 75 | 1.7 | 20 | 35 |
| | Calcium acetate | 0.03 | 72 | 1.7 | 66 | 83 |
| | Calcium chloride | 0.03 | 75 | 1.7 | 70 | 85 |
| Invention | Magnesium carbonate | 0.03 | 81 | 1.3 | 90 | 93 |
| | Magnesium chloride | 0.03 | 82 | 1.2 | 92 | 93 |
| | Magnesium sulfate | 0.03 | 84 | 1.2 | 98 | 97 |
| | Magnesium acetate | 0.03 | 85 | 1.1 | 100 | 100 |
| | Magnesium lactate | 0.03 | 84 | 1.2 | 95 | 96 |
| | Magnesium | 0.03 | 83 | 1.2 | 97 | 98 |

Table 1-continued

| Salts | Concentration of salts (M) | Kallidinogenase-containing aqueous extract | | | Heat-stability of kallidinogenase (relative residual activity, %) |
| --- | --- | --- | --- | --- | --- |
| | | Separability (%) | Turbidity (O.D.600) | Relative kallidinogenase activity (%) | |
| propionate Magnesium butyrate | 0.03 | 83 | 1.2 | 94 | 95 |
| Magnesium succinate | 0.03 | 81 | 1.2 | 91 | 93 |

The heat stability of kallidinogenase is that of purified kallidinogenase maintained at 55° C. and a pH of 6.0 for 60 minutes, and expressed as a relative residual activity (%) with the residual activity of kallidinogenase obtained in the presence of magnesium acetate taken as 100%.

The separability (%) represents the percentage of the amount of the extract based on the total amount of the liquid treated. The turbidity of the extract is measured at 660 m$\mu$ (nm). The activity is the BAEE (benzoyl arginine ethyl ester) decomposing activity of the extract measured in the presence of a 0.02% soybean trypsin inhibitor. The BAEE decomposing activity of the extract obtained in the presence of magnesium acetate is taken as 100%, and the measured value is converted on this basis. One BAEE unit is the amount of kallidinogenase required to decompose 1 $\mu$ of BAEE per minute when the kallidinogenase is caused to act on BAEE at 37° C.

The extract obtained in the presence of magnesium acetate is well dialyzed. The kallidinogenase unit (KU) of the dialyzate as measured by the increase of blood flow method (see, Hiroshi Moriya, "Basic Lectures in the Development of Medicines", Vol. 5, Pharmacological tests, page 974, a Japanese-language publication published in 1971 by Chijin Shokan Company, Tokyo) is 75,000 per kilogram of the raw pancreas.

The effect of salts used for extracting kallidinogenase from a powder or a water extract of pig pancreas has been found to be of the same tendency as in the case of using the raw pancreas, described above.

Preferably, the amount of the water-soluble magnesium-acid salt is such that the concentration of this salt is at least about 0.02 mole, and usually about 0.02 to about 1 mole. A suitable concentration can be chosen within this range according to the type of the salt to be used. The salt can be used in higher concentrations, but no appreciable increase in effect can be obtained with an increase in concentration. When the concentration of the salt is less than about 0.02 mole, the kallidinogenase extracting efficiency becomes poor, and the separability of the kallidinogenase-containing aqueous phase from undesired components is poor. Furthermore, this leads to an increase in the amount of protein dissolved in the aqueous extract. Accordingly, the post-treatment of the aqueous extract becomes complicated, and the yield of kallidinogenase tends to decrease.

According to a second aspect of this invention, there is provided a method for purifying kallidinogenase which comprises subjecting a kallidinogenase-containing aqueous extract obtained from the pancreas of a mammal to an adsorption-elution treatment using an anion-exchange resin, wherein said kallidinogenase-containing aqueous extract is brought into contact with a gel-type weakly basic anion-exchange resin to cause the kallidinogenase fraction to be adsorbed to said resin, and the kallidinogenase is eluted with an aqueous solution of an ammonium salt of a weak acid, thereby to collect the kallidinogenase.

This purifying method is especially suitable for obtaining purified kallidinogenase from the aqueous extract obtained by the method of this invention. It can also be applied with equally superior purifying effects to kallidinogenase-containing extracts obtained by any other methods.

The aqueous kallidinogenase-containing extract obtained by the extracting method of this invention can also be purified by an adsorption-elution procedure using silica gel, other known polysaccharide non-resinous material, as an adsorbent, or other ion-exchange resins.

We found that with a macroporous strongly basic anion-exchange resin and a macroporous weakly basic anion-exchange resin, the elution of kallidinogenase adsorbed thereto is slow, and for complete elution and separation, a large quantity of solvent and a long period of time are required, and moreover, the impurities tend to accompany the separated kallidinogenase; but that by using the gel-type weakly basic anion-exchange resin, the intended kallidinogenase adsorbed thereto can be very rapidly eluted using an aqueous solution of an ammonium salt of a weak acid as an eluting solvent, and can be easily separated from the impurities.

According to the purifying method of this invention, the kallidinogenase-containing aqueous extract is passed through a column of the gel-type weakly basic anion-exchange resin to ensure contacting between the aqueous extract and the ion-exchange resin, and thereby to adsorb the kallidinogenase fraction to the ion exchange resin. Preferably, the adsorption operation is carried out at a pH of more than about 4 but below about 8, more preferably about 5 to about 7, especially preferably about 6 ± 0.5. At pH values outside the specified range, the kallidinogenase is deactivated, and at a pH of more than about 8, the amount of kallidinogenase not adsorbed increases. Consequently, the yield and purity of the kallidinogenase are reduced.

The kallidinogenase adsorbed to the gel-type weakly basic anion-exchange resin is eluted using an aqueous solution of an ammonium salt of a weak acid at a pH of about 6 to about 7. The temperature at which the adsorption and elution are carried out may be any temperature at which kallidinogenase does not decompose. Usually, these operations are performed at room temperature. The salt can be removed from the eluate by such means as dialysis or ultrafiltration, and the resulting product can be dried at a temperature below the decomposition temperature of the kallidinogenase, usually below about 60° C. The drying can be done, for example, by lyophilizing or spray-drying techniques.

invention as a method for detecting a kininase fraction in chromatography.

Table 2

| | Invention | | Comparison 1 | | Comparison 2 | | Comparison 3 | |
|---|---|---|---|---|---|---|---|---|
| Ion exchange resin | DIAION WA 10 | | DIAION WA 30 | | DIAION SA 21A | | DIAION HPA 10 | |
| Characteristics of the ion exchange resin | weakly basic, gel-type | | weakly basic, macroporous | | strongly basic, gel-type | | strongly basic, macroporous | |
| Amount of the extract of the pig pancreas | 300 ml | | 300 ml | | 300 ml | | 300 ml | |
| Enzymes | KA* | CPase | KA | CPase | KA | CPase | KA | CPase |
| Amount adsorbed | 800 | 39000 | 900 | 107000 | 800 | 50000 | 900 | 88000 |
| Amount of the enzymes eluted during washing | 0 (0) | 38400 (98) | 0 (0) | 31200 (29) | 0 (0) | 15000 (30) | 0 (0) | 80000 (91) |
| Amount 1st fraction of the enzyme eluted 1st to 16th test tubes (0 – 304 ml.) | 790 (99) | 250 (0.6) | 190 (21) | 61360 (57) | 92 (11) | 890 (2) | 420 (47) | 3000 (3) |
| 2nd fraction 17th to 46th test tubes (305 – 874 ml.) | 0 (0) | 0 (0) | 405 (45) | 14250 (13) | 0 (0) | 0 (0) | 380 (42) | 2000 (2) |
| 3rd fraction 47th to 96th test tubes (875 – 1,824 ml.) | 0 (0) | 0 (0) | 300 (33) | 144 (0.1) | 0 (0) | 0 (0) | 50 (6) | 0 (0) |

*KA stands for kallidinogenase.

The gel-type weakly anion-exchange resin used in the performance of the above purifying method is preferably a resin having a secondary or tertiary amine as an exchange group, examples of which are divinylbenzene acrylate type resin (DIAION WA 10, DIAION WA 11, trademarks for products of Mitsubishi Chemical Industries Ltd., Japan), and styrene divinylbenzene type resins (AMBERLITE IR 45, AMBERLITE IRA 47, AMBERLITE IRX 68, trademarks for products of Rhom & Haas Co., U.S.A.).

In order to demonstrate the effect of the gel-type weakly basic anion-exchange resin, the following experiment was performed using DIAION WA 10 as the gel-type weakly basic anion-exchange resin in accordance with this invention, and as other anion-exchange resins, a macroporous weakly basic anion-exchange resin (DIAION WA 30, trademark for a product of Mitsubishi Chemical Industries, Ltd.), a gel-type strongly basic anion-exchange resin (DIAION SA 21A, trademark for a product of Mitsubishi Chemical Industries, Ltd.), and a Macroporous strongly basic anion-exchange resin (DIAION HPA 10, trademark for a product of Mitsubishi Chemical Industries, Ltd.)

The experimental procedure comprises passing 300 ml. of an extract of the raw pancreas of a pig (3 BAEE units/ml. as kallidinogenase) through a column (3 × 25 cm) of each of the ion-exchange resins mentioned above, washing the resin with a 0.2M solution of ammonium acetate (pH 6.0), and eluting the extract using a 0.4M solution of ammonium acetate (pH 6.0) at a flow rate of 50 ml/hr while collecting the eluate in fractions each with a volume of 19 ml. per test tube. The results are shown in Table 2.

Referring to Table 2, the kallidinogenase is expressed by BAEE units.

The carboxypeptidase (CPase) is expressed by HPLA (hippuryl-L-$\beta$-phenyl lactate) decomposing activity. One HPLA unit is the amount of CPase required to decompose $1\mu$ mole of HPLA per 1 minute when CPase is caused to act on HPLA. The measurement of the HPLA decomposing activity is employed in this invention as a method for detecting a kininase fraction in chromatography.

The figures in the parentheses represent the percentages of the amount of the eluted enzyme based on the amount of the enzyme adsorbed to the ion exchange resin.

The biological activity of the kallidinogenase in those eluted fractions which had BAEE decomposing activity was ascertained by the increase of blood flow method, and the biological activity of the kininase in those eluted fractions which had HPLA decomposing activity was ascertained by a rat uterus smooth muscle shrinking method (see Hiroshi Moriya, "Basic Lectures in the Development of Medicines", Vol. 5, Pharmacological Test Methods, page 974, a Japanese-language publication published by Chijin Shokan Company, Tokyo in 1971).

It can be seen from the results shown in Table 2 that according to the purifying method of this invention using the gel-type weakly basic anion-exchange resin, about 99% of kallidinogenase was eluted and recovered in the first fraction of 304 ml, and the eluting and recovering efficiency was far superior to those obtained in the case of using the gel-type strongly basic anion-exchange resin, the macroporous strongly basic anion-exchange resin, and the macroporous weakly basic anion-exchange resin. The results also demonstrate that the amount of CPase, an undesirable impurity, is far smaller in the invention than in the comparison runs; at the time of washing the resin before elution, a greater part (98%) of the adsorbed CPase can be removed; substantially all (99%) of the kallidinogenase can be eluted and recovered at the early stage of elution; and that the amount of CPase is very small (0.6%), and the quality of the purified kallidinogenase obtained by one cycle of the adsorption-elution procedure has very good quality.

The following Examples illustrate the present invention in greater detail. In these examples, the essential pancreas contents were about 50% by weight based on the pancreas used. The pancreas was used without removing the fat.

The kininase activity is expressed by kininase units. One kininase unit is the amount of kininase required to decompose 1 ng of bradykinin per minute.

EXAMPLE 1

500 g of raw pancreas of pig was minced, and 2,000 ml. of water was added. The pH of the mixture was adjusted to 6.0. 12 g (concentration 0.05M) of magnesium sulfate was added to the above mixture, and they were well mixed. The mixture was allowed to stand at about 50° C. for 1.5 hours. The extract separated as a bottom layer was taken out, and kallidinogenase was obtained in an amount corresponding to 36,000 kallidinogenase units (KU).

EXAMPLE 2

500 g of raw pancreas of pig was minced, and 2,000 ml. of water was added. The pH of the mixture was adjusted to 6.0. 13 g (concentration 0.03 M) of magnesium acetate was added to the mixture, and they were well mixed. The mixture was allowed to stand at about 55° C. for 1 hour. The extract separated as a bottom layer was taken out, and kallidinogenase was obtained in an amount corresponding to 37,000 KU.

EXAMPLE 3

100 g of an acetone-dried powder of the pancreas of pig was mixed with 3,000 ml. of water, and the pH of the mixture was adjusted to 6. 16 g (concentration 0.025 M) of magnesium acetate was added to the mixture, and they were well mixed. The mixture was allowed to stand at about 50° C. for 1.5 hours. The extract separated as a bottom layer was taken out, and kallidinogenase was obtained in an amount corresponding to 73,000 KU.

EXAMPLE 4

3,000 ml. of water was added to 100 g of a water extract of the pancreas of pig, and the pH of the mixture was adjusted to 6. 18 g (concentration 0.05 M) of magnesium sulfate was added to the mixture, and they were well mixed. The mixture was allowed to stand at about 47° C. for 2 hours. The extract separated as a bottom layer was taken out, and kallidinogenase was obtained in an amount corresponding to 72,000 KU.

EXAMPLE 5

300 g of raw pancreas of pig was minced, and 900 ml. of water was added and the pH of the mixture was adjusted to 6. 6.25 g (concentration 0.03 M) of Magnesium acetate was added to the mixture, and they were well mixed. The mixture was allowed to stand at about 50° C. for 1.5 hours. The mixture was allowed to stand at room temperature to remove the top layer containing fat. The bottom layer was subjected to centrifugal separation to obtain 800 ml of the extract. The extract was passed through a column (3 × 25 cm) of a gel-type weakly basic anion-exchange resin (DIAION WA 10) buffered with a 0.15 M solution of ammonium acetate (pH 6.0), and after washing the resin with a 0.2 M solution of ammonium acetate (pH 6.0), the extract was eluted with a 0.4 M solution of ammonium acetate (pH 6.0).

The salt was removed from the eluate, and the resulting kallidinogenase fraction was lyophilized to obtain 148 mg (117.7 KU/mg) of kallidinogenase. The kininase unit of this product per kallidinogenase unit (KU) was only 0.5.

EXAMPLE 6

30 g of an acetone-dried powder of the pancreas was mixed well with 20 times its amount of water and the pH of the mixture was adjusted to 6. 3.2 gram (concentration 0.05 M) of magnesium sulfate was added to the mixture, and they were well mixed. The mixture was allowed to stand at about 45° C. for 2 hours. The mixture was then allowed to stand at room temperature, and the top layer containing solids such as insoluble protein was removed. The bottom layer was subjected to centrifugal separation to obtain 550 ml of the extract. The extract was passed through a column (3 × 25 cm) of a gel-type weakly basic anion-exchange resin (AMBERLITE IRX 68) buffered with a 0.15 M solution of ammonium acetate (pH 6.0), and after washing the resin with 600 ml. of a 0.2 M solution of ammonium acetate (pH 6.0), the extract was eluted with a 0.4 M solution of ammonium acetate (pH 6.0).

The salt was removed from the eluate, and the resulting kallidinogenase fraction was lyophilized to obtain 156 mg (142.3 KU/mg) of kallidinogenase. The kininase unit of this product per kallidinogenase unit (KU) was only 1.

EXAMPLE 7

The extracts obtained in Example 1 and Example 2 were each eluted and dried in the same way as in Example 5 to obtain 257 mg and 241 mg, respectively, of kallidinonase. The kallidinogenase activities were 108.3 KU/mg and 126.2 KU/mg, respectively.

EXAMPLE 8

The extract obtained in Example 3 was eluted and dried in the same way as in Example 6 to obtain 355 mg of kallidinogenase. The kallidinogenase activity of this product was 98.5 KU/mg.

What we claim is:
1. A method for extracting and collecting kallidinogenase (EC 3.4.4.21 substance) which comprises extracting the pancreas of a mammal with water in the presence of a salt at a temperature of about 45° to about 60° C. and a pH of about 5 to about 8, wherein the extraction is carried out in the presence of a water-soluble salt of magnesium with an acid to extract and collect kallidinogenase.
2. The method of claim 1 wherein said water-soluble magnesium salt is selected from the group consisting of mineral acid salts of magnesium and $C_1$–$C_5$ fatty acid salts of magnesium.
3. The method of claim 1 wherein the concentration of the salt is about 0.02 to about 1 mole per liter of water.
4. The method of claim 2 wherein said water-soluble magnesium salt is selected from the group consisting of magnesium carbonate, magnesium chloride, magnesium nitrate, magnesium sulfate, magnesium formate, magnesium acetate, magnesium propionate, magnesium butyrate, magnesium lactate, magnesium maleate, magnesium oxalate, magnesium succinate and magnesium valerate.

* * * * *